(12) United States Patent
Malhi et al.

(10) Patent No.: US 9,072,867 B2
(45) Date of Patent: Jul. 7, 2015

(54) CATHETER WITH EXTERNAL FLOW CHANNEL (75) Inventors: Arnaz S. Malhi, Watertown, MA (US); Richard M. Braga, North Easton, MA (US)

(73) Assignee: Covidien LP, Mansfield, MA (US)

( * ) Notice: Subject to any disclaimer, the term of this patent is extended or adjusted under 35 U.S.C. 154(b) by 167 days.

(21) Appl. No.: 13/250,144

(22) Filed: Sep. 30, 2011

(65) Prior Publication Data
US 2013/0085478 A1    Apr. 4, 2013

(51) Int. Cl.
*A61M 25/00* (2006.01)
*A61M 1/36* (2006.01)

(52) U.S. Cl.
CPC .......... *A61M 25/007* (2013.01); *A61M 25/0029* (2013.01); *A61M 25/0028* (2013.01); *A61M 25/0068* (2013.01); *A61M 1/3653* (2013.01); *A61M 2025/0031* (2013.01); *A61M 1/3661* (2014.02)

(58) Field of Classification Search
CPC .......... A61M 25/0029; A61M 25/007; A61M 1/3661; A61M 25/0068; A61M 25/0028; A61M 1/3653; A61M 2025/0031
USPC ...................... 604/523, 39–43, 264
See application file for complete search history.

(56) References Cited

U.S. PATENT DOCUMENTS

| 701,075 | A | 5/1902 | McCully |
|---|---|---|---|
| 2,541,691 | A | 2/1951 | Eicher |
| D208,838 | S | 10/1967 | St. Amand |
| 4,134,402 | A | 1/1979 | Mahurkar |
| D254,270 | S | 2/1980 | Ziegler |
| 4,391,276 | A | 7/1983 | Lazarus et al. |
| 4,403,983 | A | 9/1983 | Edelman et al. |
| D272,651 | S | 2/1984 | Mahurkar |
| 4,443,333 | A | 4/1984 | Mahurkar |
| 4,493,696 | A | 1/1985 | Uldall |
| 4,568,329 | A | 2/1986 | Mahurkar |
| 4,583,968 | A | 4/1986 | Mahurkar |
| 4,601,697 | A | 7/1986 | Mammolenti et al. |
| 4,604,379 | A | 8/1986 | Twardowski et al. |

(Continued)

FOREIGN PATENT DOCUMENTS

| CA | 2 326 941 | 10/1976 |
|---|---|---|
| CA | 2 389 227 | 10/2001 |

(Continued)

OTHER PUBLICATIONS

Bard Access Systems Power-Trialysis Short-Term Dialysis Catheter—Short-Term Triple Lumen Dialysis Catheter, Enhanced Acute Dialysis Care, Nov. 3, 2011.

(Continued)

*Primary Examiner* — Theodore Stigell
*Assistant Examiner* — Lauren M Peng
(74) *Attorney, Agent, or Firm* — John Paul Mello, Esq.

(57) ABSTRACT

A catheter is provided which includes a body having a proximal end, a distal end and a sidewall defining at least one lumen. The catheter body has at least one side opening formed through the sidewall at a location spaced proximally from the distal end. The at least one side opening communicates with the at least one lumen. A recess extends along the sidewall and communicates with the at least one side opening such that the recess defines a fluid pathway into the side opening.

12 Claims, 6 Drawing Sheets

(56) References Cited

U.S. PATENT DOCUMENTS

| | | |
|---|---|---|
| 4,619,643 A | 10/1986 | Bai |
| 4,626,240 A | 12/1986 | Edelman et al. |
| 4,643,711 A | 2/1987 | Bates |
| D289,682 S | 5/1987 | Dragan |
| 4,675,004 A | 6/1987 | Hadford et al. |
| 4,682,978 A | 7/1987 | Martin |
| 4,687,471 A | 8/1987 | Twardowski et al. |
| 4,692,141 A | 9/1987 | Mahurkar |
| D292,825 S | 11/1987 | Dragan |
| 4,769,005 A | 9/1988 | Ginsburg et al. |
| 4,770,652 A | 9/1988 | Mahurkar |
| 4,772,268 A | 9/1988 | Bates |
| 4,772,269 A | 9/1988 | Twardowski et al. |
| D298,461 S | 11/1988 | Manno |
| 4,795,439 A | 1/1989 | Guest |
| 4,808,155 A | 2/1989 | Mahurkar |
| 4,808,156 A | 2/1989 | Dean |
| 4,842,582 A | 6/1989 | Mahurkar |
| 4,894,057 A | 1/1990 | Howes |
| 4,895,561 A | 1/1990 | Mahurkar |
| 4,897,079 A | 1/1990 | Zaleski et al. |
| 4,904,238 A * | 2/1990 | Williams ................. 604/43 |
| 4,961,809 A | 10/1990 | Martin |
| D312,872 S | 12/1990 | Mähl |
| 4,995,865 A | 2/1991 | Gahara et al. |
| 5,009,636 A | 4/1991 | Wortley et al. |
| 5,015,184 A | 5/1991 | Perry et al. |
| 5,035,399 A | 7/1991 | Rantanen-Lee |
| 5,041,083 A | 8/1991 | Tsuchida et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,135,599 A | 8/1992 | Martin et al. |
| 5,156,592 A | 10/1992 | Martin et al. |
| 5,167,623 A | 12/1992 | Cianci et al. |
| 5,171,218 A | 12/1992 | Fonger et al. |
| 5,171,227 A | 12/1992 | Twardowski et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A | 6/1993 | Mahurkar |
| 5,273,527 A | 12/1993 | Schatz et al. |
| 5,281,134 A | 1/1994 | Schultz |
| 5,282,788 A | 2/1994 | Wilk et al. |
| 5,290,282 A | 3/1994 | Casscells |
| 5,308,338 A | 5/1994 | Helfrich |
| 5,318,518 A | 6/1994 | Plechinger et al. |
| 5,336,165 A | 8/1994 | Twardowski |
| 5,346,471 A | 9/1994 | Raulerson |
| 5,348,536 A | 9/1994 | Young et al. |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,403,291 A | 4/1995 | Abrahamson |
| 5,405,341 A | 4/1995 | Martin |
| 5,419,777 A | 5/1995 | Hofling |
| 5,451,206 A | 9/1995 | Young |
| 5,451,216 A | 9/1995 | Quinn |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,536,234 A | 7/1996 | Newman |
| 5,549,541 A | 8/1996 | Muller |
| 5,554,136 A | 9/1996 | Luther |
| 5,556,390 A | 9/1996 | Hicks |
| 5,562,640 A | 10/1996 | McCabe et al. |
| 5,569,182 A | 10/1996 | Twardowski et al. |
| 5,571,093 A | 11/1996 | Cruz et al. |
| 5,607,440 A | 3/1997 | Danks et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,707,351 A | 1/1998 | Dorsey, III |
| 5,718,678 A | 2/1998 | Fleming, III |
| 5,725,495 A | 3/1998 | Strukel et al. |
| 5,776,092 A | 7/1998 | Farin et al. |
| 5,776,096 A | 7/1998 | Fields |
| 5,782,797 A | 7/1998 | Schweich, Jr. et al. |
| 5,785,678 A | 7/1998 | Griep et al. |
| 5,788,680 A | 8/1998 | Linder |
| 5,788,681 A | 8/1998 | Weaver et al. |
| 5,797,869 A | 8/1998 | Martin et al. |
| 5,801,012 A | 9/1998 | Soff et al. |
| 5,807,311 A | 9/1998 | Palestrant |
| 5,807,329 A | 9/1998 | Gelman |
| 5,810,789 A | 9/1998 | Powers et al. |
| 5,830,184 A | 11/1998 | Basta |
| 5,830,196 A | 11/1998 | Hicks |
| 5,858,009 A | 1/1999 | Jonkman |
| 5,868,717 A | 2/1999 | Prosl |
| 5,902,476 A | 5/1999 | Twardowski |
| 5,947,953 A | 9/1999 | Ash et al. |
| 5,961,485 A | 10/1999 | Martin |
| 5,961,486 A | 10/1999 | Twardowski et al. |
| 5,976,103 A | 11/1999 | Martin |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,063,099 A | 5/2000 | Danks et al. |
| 6,086,565 A | 7/2000 | Ouchi |
| 6,099,519 A | 8/2000 | Olsen et al. |
| 6,123,725 A | 9/2000 | Aboul-Hosn |
| 6,126,631 A | 10/2000 | Loggie |
| 6,132,616 A | 10/2000 | Twardowski et al. |
| 6,146,354 A | 11/2000 | Beil |
| 6,146,536 A | 11/2000 | Twardowski |
| 6,152,910 A | 11/2000 | Agro et al. |
| 6,156,016 A | 12/2000 | Maginot |
| 6,190,349 B1 | 2/2001 | Ash et al. |
| 6,190,357 B1 | 2/2001 | Ferrari et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,299,444 B1 | 10/2001 | Cohen |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,423,050 B1 | 7/2002 | Twardowski |
| 6,428,502 B1 | 8/2002 | Lang |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |
| 6,506,182 B2 | 1/2003 | Estabrook et al. |
| 6,517,529 B1 | 2/2003 | Quinn |
| 6,576,609 B1 | 6/2003 | Soff et al. |
| 6,579,261 B1 | 6/2003 | Kawamura |
| 6,585,705 B1 | 7/2003 | Maginot et al. |
| 6,592,542 B2 | 7/2003 | Childers et al. |
| 6,592,558 B2 | 7/2003 | Quah |
| 6,592,565 B2 | 7/2003 | Twardowski |
| 6,595,966 B2 | 7/2003 | Davey et al. |
| 6,620,118 B1 | 9/2003 | Prosl et al. |

(56) References Cited

U.S. PATENT DOCUMENTS

| | | |
|---|---|---|
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,141,035 B2 | 11/2006 | Haggstrom |
| 7,223,263 B1 | 5/2007 | Seno |
| 7,322,953 B2 | 1/2008 | Redinger |
| 7,569,029 B2 | 8/2009 | Clark |
| 2002/0121282 A1 | 9/2002 | McGuckin |
| 2003/0032918 A1 | 2/2003 | Quinn |
| 2003/0093029 A1 | 5/2003 | McGuckin, Jr. et al. |
| 2003/0100849 A1* | 5/2003 | Jang .................. 600/585 |
| 2003/0191425 A1 | 10/2003 | Rosenblatt |
| 2004/0167463 A1 | 8/2004 | Zawacki et al. |
| 2004/0249337 A1 | 12/2004 | DiFiore |
| 2005/0033222 A1 | 2/2005 | Haggstrom et al. |
| 2005/0085765 A1 | 4/2005 | Voorhees |
| 2005/0090776 A1 | 4/2005 | McGuckin, Jr. et al. |
| 2005/0177094 A1 | 8/2005 | Igarashi et al. |
| 2005/0215978 A1 | 9/2005 | Ash |
| 2005/0228339 A1 | 10/2005 | Clark |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2007/0100298 A1 | 5/2007 | Appling |
| 2008/0082080 A1 | 4/2008 | Braga |
| 2009/0054825 A1 | 2/2009 | Melsheimer et al. |
| 2009/0192435 A1* | 7/2009 | Gregersen .................. 604/6.16 |
| 2010/0069818 A1 | 3/2010 | Smouse |
| 2010/0076404 A1 | 3/2010 | Ring |
| 2010/0081986 A1 | 4/2010 | Matson et al. |
| 2011/0077577 A1 | 3/2011 | Sansoucy |
| 2011/0130745 A1 | 6/2011 | Shevgoor |

FOREIGN PATENT DOCUMENTS

| | | |
|---|---|---|
| EP | 0107810 | 5/1984 |
| EP | 0 299 622 | 1/1989 |
| EP | 0 341 721 | 11/1989 |
| EP | 0 554 722 | 8/1993 |
| EP | 0 623 356 | 11/1994 |
| EP | 0 322 225 | 2/1995 |
| EP | 0 713 406 | 3/1998 |
| EP | 0 570 530 | 8/1999 |
| EP | 0 555 780 | 9/1999 |
| EP | 1 197 239 | 4/2002 |
| EP | 1 144 039 | 12/2005 |
| EP | 1905476 A2 | 4/2008 |
| EP | 2 168 625 | 3/2010 |
| EP | 2168625 A1 | 3/2010 |
| FR | 2326941 | 6/1979 |
| GB | 1503469 | 3/1978 |
| GB | 2028136 | 3/1980 |
| JP | 08103492 | 4/1996 |
| JP | 8308933 | 11/1996 |
| JP | 2004-174130 A | 6/2004 |
| WO | WO 92/14500 | 9/1992 |
| WO | WO 95/04567 | 2/1995 |
| WO | WO 95/10317 | 4/1995 |
| WO | WO 97/37699 | 10/1997 |
| WO | WO 98/41277 | 9/1998 |
| WO | WO 99/38550 | 8/1999 |
| WO | WO 99/65557 | 12/1999 |
| WO | WO 01/91845 | 12/2001 |
| WO | WO 02/13899 | 2/2002 |
| WO | WO 02/18004 | 3/2002 |
| WO | WO 03/033049 | 4/2003 |
| WO | WO 03/066148 | 8/2003 |
| WO | WO 2004/093956 | 11/2004 |
| WO | WO 2005/023336 | 3/2005 |
| WO | WO 2005/077449 | 8/2005 |
| WO | WO 2005/084741 | 9/2005 |
| WO | WO 2006/014339 | 2/2006 |
| WO | 2008155145 A1 | 12/2008 |

OTHER PUBLICATIONS

European Search Report dated Oct. 25, 2012 in copending European Appln. No. 12183338.
EP Search Report from EP Application No. EP 12 18 4656 dated May 11, 2012.
Office Action issued in the corresponding Japanese Application No. 2012-212145 mailed Aug. 28, 2013.
Official Action issued in Japanese Appl. No. 2012-214681 dated Aug. 28, 2013.
Examiner's Report issued in Australian Appl. No. 2012230094 dated Sep. 12, 2013.
Examiner's Report issued in Australian Appl. No. 2010226891 dated Sep. 5, 2013.

\* cited by examiner

CATHETER WITH EXTERNAL FLOW CHANNEL

TECHNICAL FIELD

The present disclosure relates to catheters for use in medical procedures, and in particular, to catheters for withdrawing fluids from the body during medical procedures.

BACKGROUND

Catheters are flexible medical instruments for use in the introduction and withdrawal of fluids to and from body cavities, ducts and vessels. Catheters are used for many different applications within the human body including the administration of liquid therapeutic agents and the removal of bodily fluids for testing, monitoring, or disposal. Catheters have a particular application in hemodialysis procedures, in which blood is withdrawn from a blood vessel, directed to a hemodialysis unit for dialysis or purification, and subsequently returned to the blood vessel.

Typically, dialysis catheters define at least two lumens including a venous lumen and an arterial lumen. The arterial lumen withdraws blood from the patient and delivers the blood to a dialysis machine. The venous lumen receives blood from the dialysis machine and returns the blood to the patient. The venous and arterial lumens may include distal openings adjacent the tip of the catheter. In addition, the venous and arterial lumens may also include side openings which provide redundant or alternate flow paths to and from the arterial and venous lumens.

When a catheter is placed in a body cavity and fluid is withdrawn through a lumen of the catheter, e.g., the arterial lumen, the catheter opening or openings communicating the catheter lumen with the body cavity may become occluded. More specifically, because the catheter lumen for withdrawing fluid from a vessel draws a vacuum adjacent the openings, body tissue may be drawn into the distal and/or side openings of the arterial lumen and occlude the openings. Although the redundant flow paths created by providing both distal and side openings reduce the likelihood of total occlusion of the catheter withdrawal lumen, further improvements to known catheters to further reduce the likelihood of vessel occlusion are desirable.

Therefore, it would be desirable to overcome the disadvantages associated with known catheters by providing a catheter which is less susceptible to occlusion and capable of providing unobstructed fluid flow into the catheter.

SUMMARY

A catheter in accordance with the present disclosure includes a body having a proximal end and a distal end. The catheter body includes a sidewall defining at least one lumen and at least one side opening formed through the sidewall at a location spaced proximally from the distal end. The at least one side opening communicates with the at least one lumen. A recess extends along the sidewall and communicates with the at least one side opening to define a fluid pathway into the side opening.

In one embodiment, the body defines at least one distal opening which communicates with the at least one lumen and is positioned distally of the at least one side opening.

In one embodiment, the at least one lumen includes a first lumen and a second lumen and the at least one side opening includes first and second side openings. First and second recesses may be provided to communicate with the first and second side openings, respectively.

In one embodiment, the at least one recess is substantially linear. Alternately, the at least one recess may be non-linear.

The at least one recess may extend proximally from the at least one side opening. Alternately, the at least one recess may extend distally from the at least one side opening.

In one embodiment, the at least one recess includes a plurality of recesses communicating with each of the at least one side openings. The plurality of recess may be linear or non-linear and may extend proximally or distally from the side opening.

In one embodiment, a portion of the sidewall defining a base of the recess has a thickness which decreases in a direction towards the side opening. Similarly, a portion of the sidewall defining a base of the recess may slope downwardly towards the side opening.

In another embodiment, a portion of the sidewall defining a base of the recess includes an undulating surface.

BRIEF DESCRIPTION OF THE DRAWINGS

Various embodiments of the present disclosure will be described herein with reference to the accompanying drawings, wherein.

DETAILED DESCRIPTION OF EMBODIMENTS

Various exemplary embodiments of the presently disclosed catheter are discussed herein in terms of a hemodialysis catheter. However, it is envisioned that the principles of the present disclosure are equally applicable to a range of catheter applications such as, for example, hemodialysis, cardiac, abdominal, urinary, and intestinal, including both chronic and acute applications. Moreover, the catheter can be used for the delivery and/or withdrawal of fluids such as, for example, medication, saline, bodily fluids, blood and urine.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human patient or other animal, and the term "clinician" should be understood as referring to a doctor, nurse or other care provider and may include support personnel.

Figure 1:
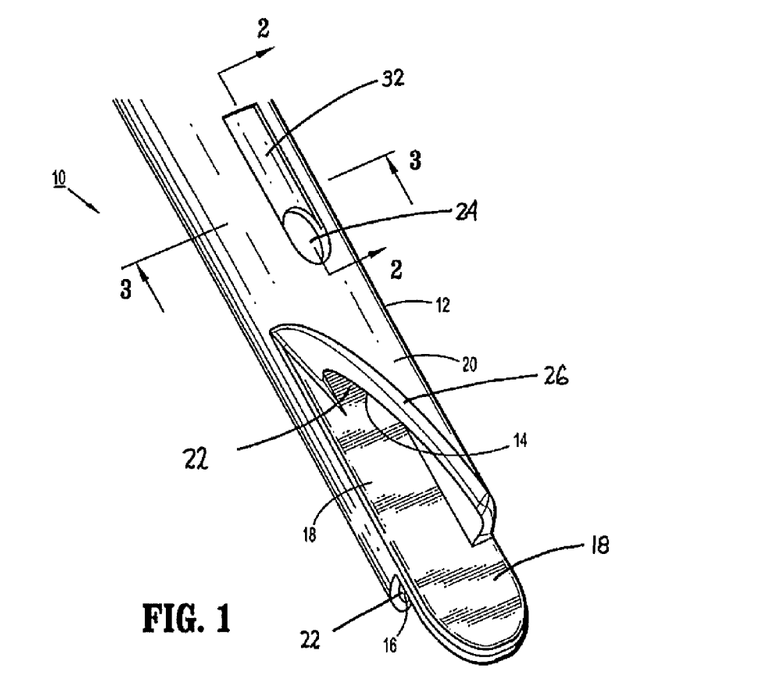
FIG. 1 is a perspective view of the distal end of one embodiment of the presently disclosed catheter.
Figure 2:
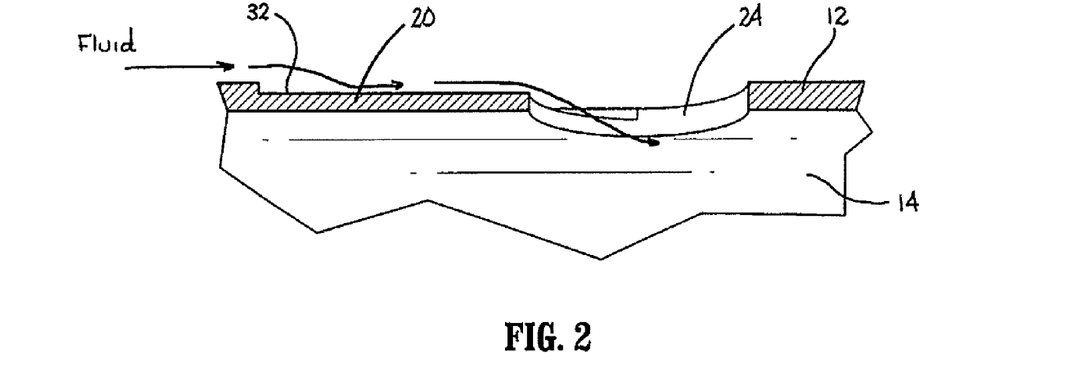
FIG. 2 is a side, cross-sectional view of a portion of the distal end of the catheter shown in FIG. 1.
Figure 2A:
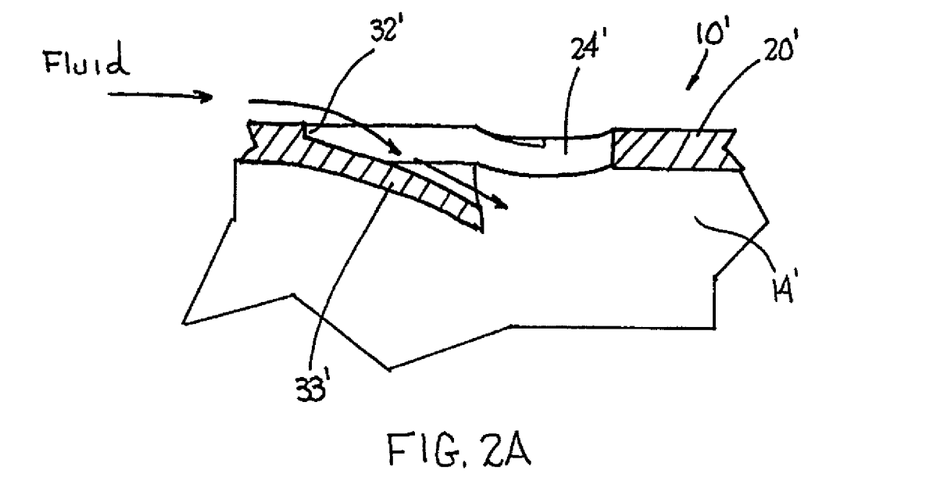
FIG. 2A is a side, cross-sectional view of a distal end of an alternative embodiment of the catheter shown in FIG. 1.
Figure 3:
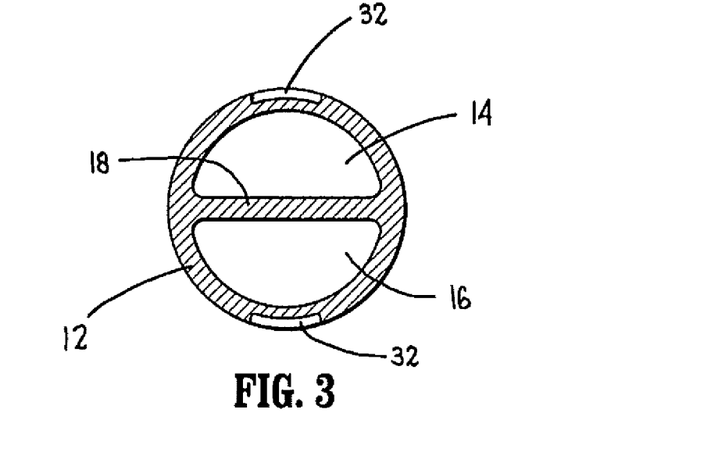
FIG. 3 is a cross-sectional view taken along section lines 3-3 of FIG. 1.

FIGS. 1-3 illustrate one embodiment of the presently disclosed catheter shown generally as 10. Catheter 10 includes a catheter body 12 defining a first lumen 14 and a second lumen 16. As illustrated, first and second lumens 14 and 16 are substantially D-shaped. Alternately, it is envisioned that lumens 14 and 16 may have a variety of configurations including circular. A septum 18 extends from the proximal end of the body 10 to the distal end of body 10. In one embodiment, the septum 18 extends distally of a distal end of the sidewalls 20 defining the outer perimeter of body 12.

Body 12 defines a pair of distal openings 22 and a pair of diametrically opposed side openings 24 which are spaced proximally of the distal openings 22. In one embodiment, each distal opening 22 is defined between septum 18 and distal spirally configured sidewall extensions 26 of sidewalls 20. A catheter including similarly configured distal sidewall extensions 26 is disclosed in U.S. Pat. No. 7,776,005 which is incorporated herein by reference in its entirety. Alternately, it is envisioned that the distal end of the catheter 10 may assume a variety of configurations known in the art.

Side openings 24 are formed through sidewalls 20 of catheter body 12 at locations spaced proximally of distal openings 22. Each opening 24 communicates with a respective one of the first and second lumens 14 and 16. As illustrated, openings 24 are positioned in diametrically opposed locations on body 10. Alternatively, openings 24 may not be diametrically opposed. Although openings 24 are illustrated as having an oval configuration, other configurations including polygonal, rectangular, square, trapezoidal, circular, and other regular and irregular shaped openings are envisioned.

As shown in FIGS. 1-3, a recess 32 is defined in sidewall 20 proximally to each side opening 24. The recess 32 may define a spherical concavity, a rectangular channel or have any desired configuration which defines a channel positioned below the outer surface of sidewall 20. Each recess 32 communicates with a side opening 24 to define an additional flow path into a respective one of first and second lumens 14 and 16. As will be discussed in further detail below, by providing an additional flow path which communicates with the side openings 24, if a side opening 24 becomes occluded, the additional flow path provides a means for maintaining the patency of the side opening 24.

In one embodiment, the length of the recess 32 is between 0.25 cm to about 3 cm. In one embodiment, the length of recess 32 is about 0.5 cm to about 1 cm. In another embodiment, the length of the recess 32 is about 2 cm.

When catheter 10 is used in a medical procedure, for example, a hemodialysis procedure, the catheter 10 is placed in a vein, typically the superior vena cava for a central venous catheter, through the internal jugular vein in the neck and advanced downwards toward the chest. The proximal end of catheter 10 is connected to a dialyzer in a known manner such that one of the first and second lumens 14 and 16 defines the arterial lumen of the catheter 10 and one of the first and second lumens 14 and 16 defines the venous lumen of the catheter 10. As discussed above, the arterial lumen is used to withdraw blood from a patient's vein and deliver the blood to a dialyzer and the venous lumen returns blood from the dialyzer to the patient's vein. Because a negative pressure is effected within the arterial lumen, tissue may be drawn into the distal opening 14, 16 and/or the side opening 24 of catheter 10 to occlude one or both the openings. In the event that tissue is drawn into the side opening 24 of the arterial lumen, the recess 32 provides an alternate flow path into the side opening 24 to maintain patency of the opening and facilitate continued flow through the side opening 24. Additionally, if the side opening 24 is resting on the vein wall and is thus occluded, the recess will provide a means to keep the side opening 24 patent.

FIG. 2A illustrates an alternate embodiment of the catheter 10 shown generally as 10'. Catheter 10' includes a sidewall 20' which defines a side opening 24'. A recess 32' is formed in sidewall 20' as discussed above with respect to recess 32 of catheter 10. In addition, the portion 33' of the sidewall 20' in which the recess 32' is formed is deformed downwardly such that an outer surface of portion 33' defines a downwardly sloped surface which is directed into side opening 24' and arterial lumen 14'. In one embodiment, catheter 10' can be formed by using a heated die to press the wall portion 33' defining a bottom of recess 32' of catheter 10 downwardly to the position shown in FIG. 2A. Alternatively, portion 33' may be formed using any know molding or machining process.

Figure 4:
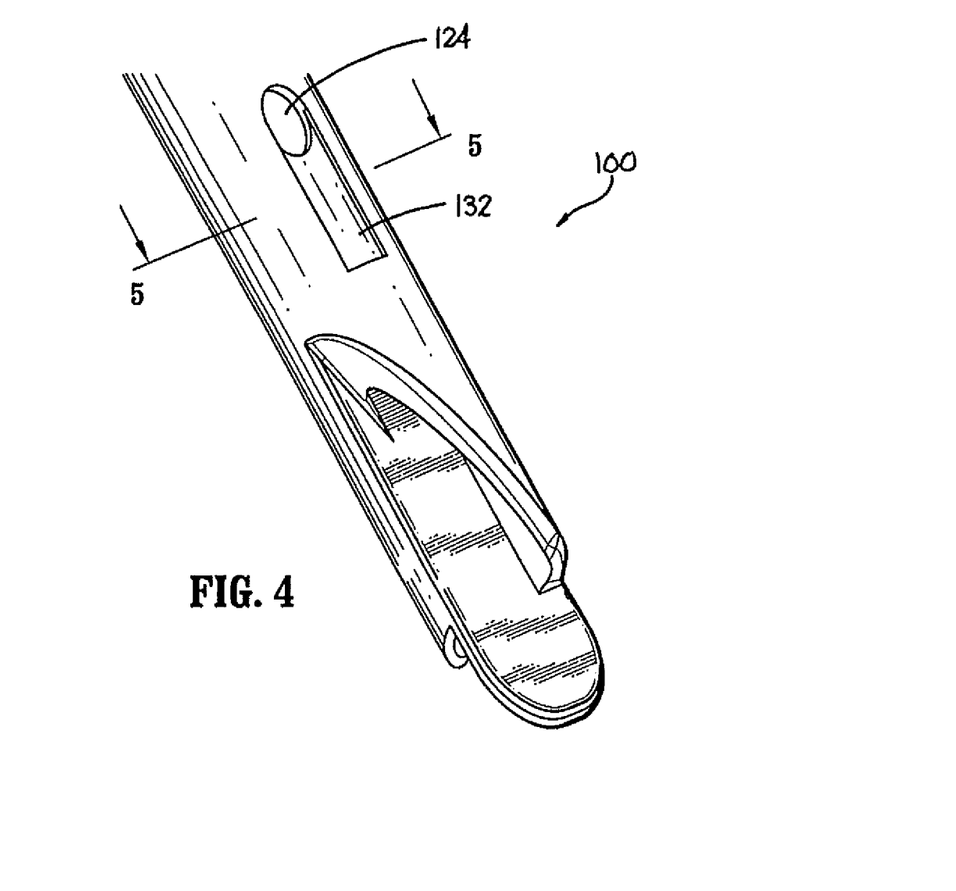
FIG. 4 is a perspective view of the distal end of another embodiment of the presently disclosed catheter.
Figure 5:
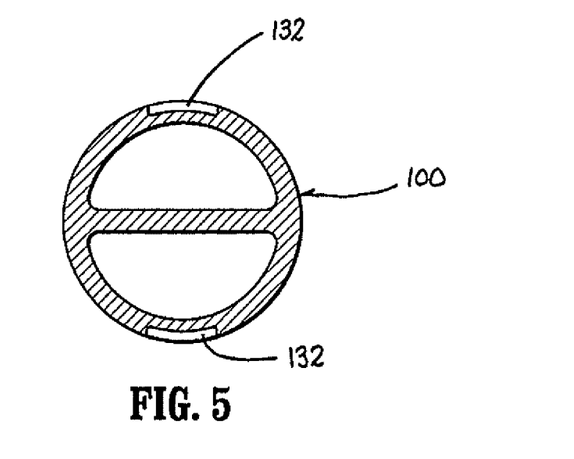
FIG. 5 is a cross-sectional view taken along section lines 5-5 of FIG. 4.

FIGS. 4 and 5 illustrate an alternate embodiment of the presently disclosed catheter shown generally as 100. Catheter 100 is substantially similar to catheter 10 in all respects except that recess 132 is positioned distally of side opening 124 between the distal end of catheter 100 and side opening 124.

Figure 6:
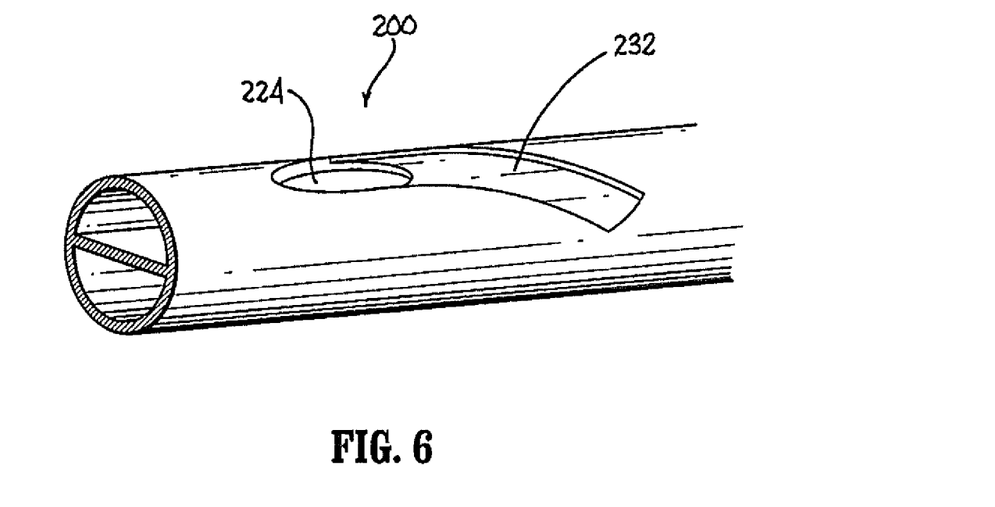
FIG. 6 is a side perspective view of the distal end of yet another embodiment of the presently disclosed catheter.

FIG. 6 illustrates another alternate embodiment of the presently disclosed catheter shown generally as 200. Catheter 200 is substantially similar to catheter 10 in that catheter 200 includes a recess 232 which is positioned proximally of side opening 224. However, in contrast to catheter 10, the recess 232 is non-linear or curved. Although not shown, the curved recess 232 may also be positioned distally of side opening 224. Curving the recess 232 may further enhance the benefits of preventing total occlusion by locating a portion of the recess 232 further from the vessel tissue. This may be especially true in case where the side opening 224 is resting on the vein wall.

Figure 7:
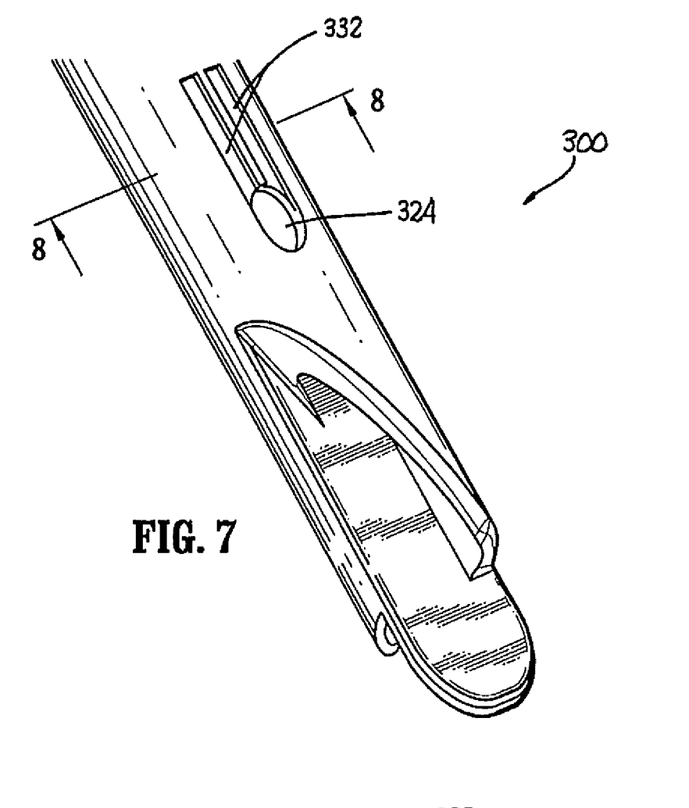
FIG. 7 is a perspective view of the distal end of another embodiment of the presently disclosed catheter.
Figure 8:
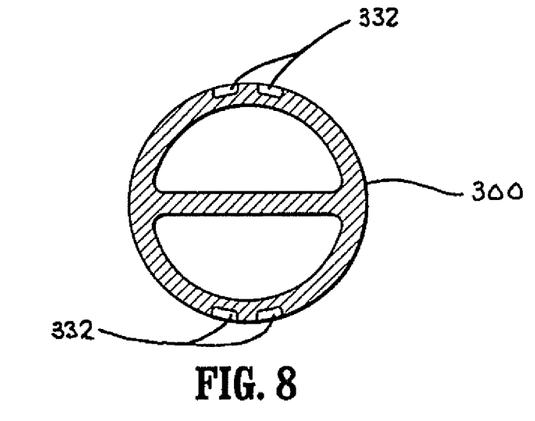
FIG. 8 is a cross-sectional view taken along section lines 8-8 of FIG. 7.
Figure 9:
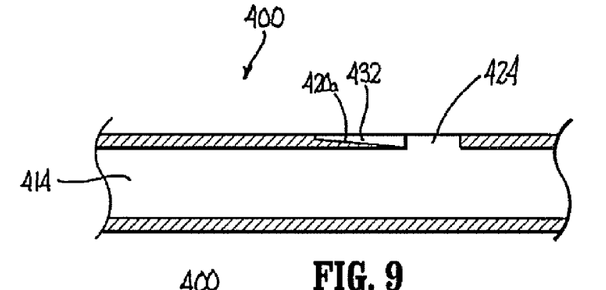
FIG. 9 is a side cross-sectional view of a distal portion of another embodiment of the presently disclosed catheter.
Figure 9A:
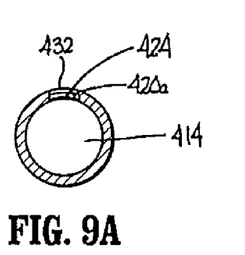
FIG. 9A is a transverse cross-sectional view of the catheter of FIG. 9.

In yet another alternative embodiment shown in FIGS. 7 and 8, catheter 300 includes a plurality of spaced recesses 332 which are positioned proximally of and communicate with the side opening 324. Although two recesses 332 are illustrated, it is envisioned that a multiplicity of recesses 332 may be provided either distally, proximally, or both distally and proximally of each side opening 324. In addition, it is envisioned that one or more of the multiplicity of recesses 332 may be curved, linear or any combination of curved and linear.

In another alternative embodiment shown in FIGS. 9-11A, the catheter 400 which is illustrated as a single lumen catheter, includes a side opening 424 and a recess 432 positioned proximally of the side opening 424. Catheter 400 differs from catheter 10 above in that the portion of sidewall 420 defining the bottom wall 420a of recess 432 is tapered downwardly in a distal direction towards side opening 424, i.e., the thickness of the sidewall 420 at the base of the recess 432 decreases in the distal direction. Such a configuration enables the bottom wall 420a to flex slightly inwardly (FIG. 10) into lumen 414 when lumen 414 functions as the arterial lumen or flex slightly outwardly (FIG. 11) when lumen 414 functions as the venous lumen. The flexibility of bottom wall 420a of recess 432 allows fluid to more smoothly flow into and out of catheter 400 during use. The thicker proximal portion of bottom wall 420 adds some rigidity to the bottom wall 420a to limit the degree to which the bottom wall 420a is able to flex.

Figure 10:
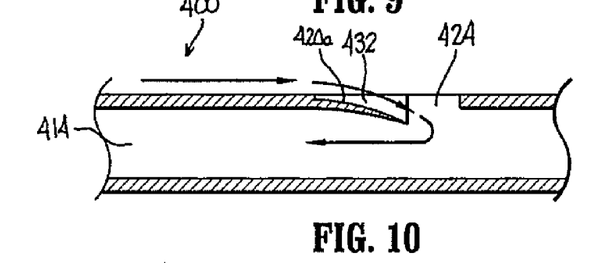
FIG. 10 is a side cross-sectional view of the catheter shown in FIG. 9 as fluid enters the catheter through the side opening.
Figure 10A:
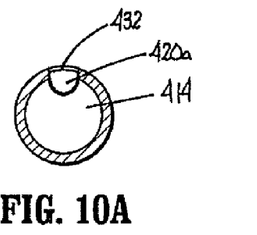
FIG. 10A is a transverse cross-sectional view of the catheter of FIG. 10.
Figure 11:
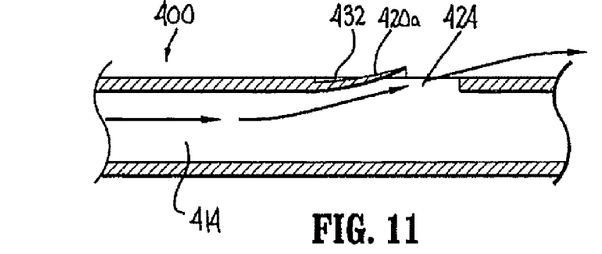
FIG. 11 is a side cross-sectional view of the catheter shown in FIG. 9 as fluid is discharged from the side opening of the catheter.
Figure 11A:
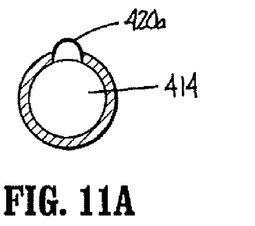
FIG. 11A is a transverse cross-sectional view of the catheter of FIG. 11.
Figure 12:
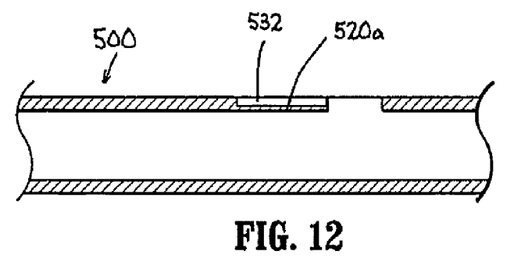
FIG. 12 is a side cross-sectional view of a distal portion of another embodiment of the presently disclosed catheter.

As shown in yet another embodiment of the presently disclosed catheter shown generally as 500, the entire length of bottom wall 520a defining recess 532 can be thinned to provide a greater flexibility to the bottom wall 520a to enable the bottom wall 520a to flex as shown in FIGS. 10-11A. Although catheters 400 and 500 are illustrated as single lumen catheters, it is envisioned that the advantages discussed above with respect to catheters 400 and 500 are equally applicable to dual lumen catheters such as shown in FIGS. 1-8 of this application.

Although not explicitly shown in the drawings, it is envisioned that the bottom wall defining the recess in any one or all of the embodiments disclosed herein may be non-linear in a longitudinal or transverse direction. For example, the bottom wall defining the recess may be undulating or have a wave-like or irregular configuration in the longitudinal and/or transverse direction. It is envisioned that such non-linear surface configurations may further minimize the likelihood of occlusion of the side opening.

Although each of the catheter embodiments discussed above describes the recesses as being associated with each of the diametrically located side openings, it is envisioned that the recess may be associated with only a single side opening. Thus, in a non-reversible dialysis catheter, the recess may be associated only with the side opening which communicates with the arterial lumen.

Although the illustrated embodiments include both distal openings and side openings, it is envisioned that the catheter may include only side openings which have recesses associated with one or both of the side openings. In addition, although this disclosure illustrates embodiments of a dual lumen catheter, it is also envisioned that the combination of a side opening and a recess is applicable to a single lumen catheter.

In addition to the advantages described above with regard to providing a recess that communicates with a side opening, it is also believed that such a configuration provides further advantages. More specifically, the provision of a recess that communicates with a side opening results in smoother flow dynamics, i.e., less flow disruption, into the side opening. By providing smoother flow dynamics into the side opening, undue shear stress on the fluid, e.g., blood, is minimized resulting in minimized platelet aggravation and reduced thrombus. To maximize these additional advantages in a dialysis catheter, the recess may be positioned proximally of the side opening communicating with the arterial lumen.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A catheter comprising:
a body defining a longitudinal axis having a proximal end and a distal end, the body including a sidewall defining at least one lumen and at least one side opening formed through the sidewall at a location spaced proximally from the distal end, the at least one side opening communicating with the at least one lumen, and further including a non-linear recess extending along the sidewall and having a uniform depth along a length of the recess extending from a first end spaced from the side opening to a second end terminating at the side opening, the recess defining a fluid pathway into the side opening.

2. The catheter according to claim 1, wherein the body defines at least one distal opening which communicates with the at least one lumen, the at least one distal opening being positioned distally of the at least one side opening.

3. The catheter according to claim 2, wherein the at least one lumen includes a first lumen and a second lumen.

4. The catheter according to claim 3, wherein the at least one side opening includes a first side opening and a second side opening.

5. The catheter according to claim 4, wherein the recess includes first and second recesses, the first and second recesses communicating with the first and second side openings, respectively.

6. The catheter according to claim 2, wherein the at least one recess extends proximally from the at least one side opening.

7. The catheter according to claim 6, wherein the at least one recess includes a plurality of recesses communicating with the at least one side opening.

8. The catheter according to claim 2, wherein the at least one recess extends distally from the at least one side opening.

9. The catheter according to claim 8, wherein the least one recess includes a plurality of recesses communicating with the at least one side opening.

10. The catheter according to claim 1, wherein the at least one recess has a length of about 0.5 cm to about 1.0 cm.

11. The catheter according to claim 1, wherein the entire recess is proximal to the side opening.

12. The catheter according to claim 1, wherein the entire recess is distal to the side opening.

* * * * *